United States Patent [19]

Wood et al.

[11] Patent Number: 4,973,326
[45] Date of Patent: Nov. 27, 1990

[54] DISPOSABLE DIAPER WITH IMPROVED FASTENER ATTACHMENT

[75] Inventors: Leigh E. Wood; John A. Miller, both of Woodbury; Alan J. Sipinen, Maplewood; Susan K. Nestegard, Woodbury, all of Minn.

[73] Assignee: Minnesota Mining and Manufacturing Company, Saint Paul, Minn.

[21] Appl. No.: 126,746
[22] Filed: Nov. 30, 1987
[51] Int. Cl.⁵ .............................................. A61F 13/16
[52] U.S. Cl. ...................................... 604/391; 24/450
[58] Field of Search ..................... 604/366, 389, 391; 24/448, 450; 128/DIG. 15, 849

[56] References Cited

U.S. PATENT DOCUMENTS

| | | | |
|---|---|---|---|
| 3,694,867 | 10/1972 | Stumpf | 24/204 |
| 3,773,580 | 11/1973 | Provost | 24/448 |
| 3,849,840 | 11/1974 | Yamada et al. | 24/450 |
| 3,923,931 | 12/1975 | Fechillas | 604/366 |
| 4,216,257 | 8/1980 | Schams et al. | 24/448 |
| 4,290,174 | 9/1981 | Kalleberg | 24/448 |
| 4,402,690 | 9/1983 | Redfern | 604/391 |
| 4,540,415 | 9/1985 | Korpman | 604/389 |
| 4,617,022 | 10/1986 | Pigneul et al. | 604/391 |
| 4,646,397 | 3/1987 | Yoshida | 24/448 |
| 4,704,117 | 11/1987 | Mitchell | 604/391 |
| 4,728,325 | 3/1988 | Spiller | 604/389 |
| 4,846,815 | 7/1989 | Scripps | 604/391 |

Primary Examiner—C. Fred Rosenbaum
Assistant Examiner—Shanon Rose
Attorney, Agent, or Firm—Donald M. Sell; Walter N. Kirn; William L. Huebsch

[57] ABSTRACT

A disposable garment or diaper having a fastener including fastener portions adapted for releasably mechanically engaging each other; and a bonding layer of room-temperature non-tacky thermoplastic material adhering one of the fastener portions to a thin polyolefin layer of the garment and being bonded to that polyolefin layer under heat and pressure that leaves the polyolefin layer substantially undeformed. The bonding layer holds the fastener portion to the polyolefin film with greater force than that which is required to separate the engaged fastener so that the fastener may be repetitively closed and opened.

8 Claims, 2 Drawing Sheets

DISPOSABLE DIAPER WITH IMPROVED FASTENER ATTACHMENT

TECHNICAL FIELD

The present invention concerns fasteners used on inexpensive or disposable garments such as diapers, and methods by which such fasteners are attached to such garments.

BACKGROUND ART

Various fasteners have been used on inexpensive or disposable garments such as diapers, including lengths of pressure-sensitive adhesive coated tape, snaps, and hook and loop type fasteners.

When lengths of pressure-sensitive adhesive coated tape are used, typically first end portions of the tape are adhered to the disposable garments when they are manufactured, and second end portions of the tape are adhered to the garments by the users to hold the garments in place. Typically such lengths of pressure-sensitive adhesive coated tape are cut from long yardage rolls of tape during manufacture of the disposable garments, and to facilitate unwinding of the rolls either a release coating is provided on the side of the tape opposite the pressure-sensitive adhesive or the adhesive is covered by a release liner which must be removed prior to attachment of the tape to the garments. Such lengths of pressure-sensitive adhesive coated tape have been widely used as the fasteners for disposable diapers, however the presence of relatively small amounts of contaminants such as talcum powder or baby oil either on the pressure-sensitive adhesive or on the portion of the garment to which the pressure-sensitive adhesive is to be adhered by the user greatly reduces the reliability of the fastener.

The use of hook and loop fasteners on inexpensive or disposable garments such as diapers substantially overcomes this problem of reduced fastener reliability due to contaminants such as talcum powder or baby oil, but the mating portions of such fasteners are difficult to attach with pressure-sensitive adhesive in the conventional manner by cutting and applying pressure-sensitive adhesive coated fastener portions from long yardage rolls of supply material. The pressure-sensitive adhesive will adhere to the surface of the fastener material against which it is wound on the roll unless a release coating is provided on the fastener material, which is difficult and impractical, or unless the adhesive is covered by a release liner which must be removed prior to attachment of the fasteners to a garment.

U.S. Pat. Nos. 3,694,867; 3,773,580 and 3,849,840 have described the use of a hot melt or thermoplastic adhesive for applying hook and loop type fasteners to garments, however neither describes a suitable system by which such portions of fasteners could be properly applied to many inexpensive garments such as disposable diapers which include an easily heat and pressure distorted thin polyolefin film or nonwoven layer to which the fastener must be adhered.

U.S. Pat. No. 3,694,867 to Stumpf describes mechanically releasably engageable fastener portions having backing layers of adhesive for which examples of thermoplastic resins are given, however the adhesives described are not suitable for adhesion to easily heat and pressure distorted thin polyolefin film or nonwoven layer of the type used on disposable diapers.

U.S. Pat. No. 3,773,580 to Provost describes a method for attaching a fastener to a substrate by coating the substrate with a first adhesive, heat activating a second adhesive on the fastener, and then pressing the two adhesives together to affix the fastener to the substrate. This method is not suitable for high speed production of inexpensive garments, however, because among other things, the difficulty associated with applying adhesive on the thin heat-sensitive film or nonwoven layer or substrate, and because of the cost of using two adhesive layers.

U.S. Pat. No. 3,849,840 to Yamada et al. describes using pressure-sensitive adhesive to attach "velvet type" fasteners, after indicating that applying fasteners with thermoplastic adhesive often results in damage to the fasteners "from both or either the pressure and/or the heat applied", which problem is particularly acute if the fastener is partially or totally made of heat sensitive materials such as polyolefinic materials. Additionally, damage from such heat and pressure can occur to substrates to which the fasteners are adhered, such as the easily distorted thin polyolefin film or nonwoven layers of disposable diapers to which fasteners are attached.

DISCLOSURE OF INVENTION

The present invention affords an easy and economical method for application of portions of fasteners, including hook and loop fasteners, to substrates such as the thin polyolefin film and nonwoven layers used in disposable diapers or similar disposable garments, which application may be done at high speeds under conditions of heat and pressure that do not substantially distort or disrupt these heat-sensitive layers but firmly hold the fastener portions in place to afford repeated engagement or disengagement thereof; which fastener portions can be severed and applied from long yardage rolls of fastener material without the need for a release coating or release liner on the fastener material to afford unwinding of the roll.

According to the present invention there is also provided a disposable garment or diaper comprising a heat and pressure-sensitive polyolefin outer layer; a fastener including fastener portions having mechanically engageable means along their first surfaces adapted for releasably mechanically engaging each other; and a bonding layer of room-temperature non-tacky thermoplastic material adhering a second surface of at least one of the fastener portions to the polyolefin layer and being bonded to the polyolefin layer under heat and pressure that leaves the polyolefin layer substantially undeformed, with the bonding layer holding the fastener portion to the polyolefin film with greater force than that which is required to separate the engaged fastener so that the fastener may be repetitively closed and opened.

The fastener portion with mechanically engageable means along its first surface that is adhered by the bonding layer in a disposable garment or diaper according to the present invention may be either portion of a fastener that makes releasable mechanical engagement with (rather than being adhered by an adhesive to) its mating portion, such as either portion of a snap, either portion of a fastener with self-engaging geometry, or, preferably, either portion of a hook and loop type fastener. The hook portions of such fasteners may be any of the known types having cut loops or headed stems projecting from a backing. The loop portion of such fasteners may be any of the known types typically comprising soft, flexible, sheet-like fibrous structures having a multiplicity of loops along one surface, which fibrous structures may be formed by any of several methods such as weaving, knitting, warp knitting, weft insertion knitting, stitch sewing, or the known methods for making nonwoven structures. Preferably the fastener portion is relatively thin (i.e., less than 0.3 centimeter thick) to afford long yardage rolls of the fastener material of a reasonably small diameter, and the fastener portion should provide secure but easily releasable engagement with a mating fastener portion for a reasonable number (e.g., at least 10) of engagements and disengagements.

The room-temperature non-tacky thermoplastic bonding layer should be a high-cohesive-strength, narrow-softening-range "warm-melt adhesive" that has an activation temperature (i.e., a temperature to which the adhesive must be heated before it is capable of forming a bond) of less that about 110 degrees Centigrade (and preferably less than about 95 degrees Centigrade) which activation temperature is relatively low compared to that of most thermoplastic resins, and which bonding layer has high cohesive strength beyond that available from waxes or other materials that soften at such lower temperatures, such that it will securely hold the fastener in place for a long period of time.

The bonding layer should be non-blocking, that is, lengths of fastener material from which the fastener portion can be cut that are coated with the bonding material should have the ability to remain wound in a supply roll and be stored under normal storage conditions of about 50 or 60 degrees Centigrade or less without adhesion of the bonding layer to the first surface of the fastener material over which it is wound that would prevent uniform low-force unwinding of the fastener material from the roll.

After being heated to a temperature needed for activation (e.g., between about 70 and 110 degrees Centigrade) the bonding layer should become and remain tacky for a period of time (e.g., more than 2 seconds) after the bonding layer is removed from the source of heat so that its temperature falls below that activation temperature and approaches room temperature. This property, called open time, allows time after heating of the bonding layer for application of the fastener to a substrate such as a polyolefin layer on a disposable diaper. Sufficient open time for the bonding layer is particularly desirable when it is impractical to simultaneously apply heat and pressure to the bonding layer and the polyolefin layer of a disposable garment during the production of such garments, as may often be the case when existing non-heating production machinery for applying lengths of pressure-sensitive adhesive coated tape is modified to apply the fastener portions with such bonding layers because it will usually be easier to add means to heat the bonding layer (such as a radiant heater) prior to the juncture at which the fastener portion is bonded to the polyolefin layer rather than at that juncture. An open time of more than 2 seconds (e.g., 9 seconds) should be adequate for the bonding layers of fastener portions applied by such thusly modified production machinery.

Bonding layers that exhibit the necessary properties of high cohesive strength, good bondability, low activation temperature, and sufficient open time can include from about 40% to about 100% of a thermoplastic material having a softening point of generally below 120 degrees Centigrade and preferably below 100 degrees Centigrade, and from about 60% to about 0% of a tackifying resin that has a softening point below about 105 degrees Centigrade and preferably below 95 degrees Centigrade. Suitable thermoplastic materials include ethylene and propylene based copolymers such as ethylene/vinyl acetate copolymers, ethylene/acrylic acid copolymers, and ethylene/methacrylic acid copolymers. Preferred thermoplastic materials include ethylene/vinyl acetate copolymers, especially those with a melt flow index from about 40 to about 2500, and preferably with a melt flow index between about 50 and about 1000. Such materials are available commercially as Elvax 40W, Elvax 150, Elvax 210W, Elvax 220W, Elvax 310, Elvax 410, and Elvax 4980W from E. I. DuPont de Nemours and Co. of Wilmington, Del.; Escorene UL7710 and Escorene UL7720 from Exxon Chemical Co., Houston, Tex.; and Ultrathene 639-35 and Ultrathene 649-04, available from USI Chemical Co. of Cincinnati, Ohio. Suitable tackifying resins are preferably solid or semisolid, however liquid tackifying resins can also be used. The tackifying resin, when used, should be compatible with the thermoplastic material and may include rosin esters, rosin acids, and derivatives of these; hydrogenated rosin esters and rosin acids and derivatives of these; aliphatic hydrocarbon resins; mixed aliphatic/aromatic hydrocarbon resins, polyterpene resins; resins made from the polymerization and hydrogenation of a dicyclopentadiene feed stream; polyterpene resins and aromatic-modified polyterpene resins; resins made from the polymerization and hydrogenation of a C9 hydrocarbon stream; and resins made from the polymerization and hydrogenation of a mixture of alphamethyl styrene, styrene, and vinyl toluene. Preferred tackifying resins include aliphatic hydrocarbon resins such as Escorez 1580 and Escorez 1310, available from Exxon Chemical of Houston, Tex.; Hercotac 95, available from Hercules Chemical Co. of Wilmington, Del.; and Wingtack Plus and Wingtack 95, available from the Goodyear Tire and Rubber Company of Akron, Ohio. Additional preferred solid tackifying resins include the aromatic-modified polyterpene resins such as Wingtack 86, available from Goodyear; Zonatac 105, available from Arizona Chemical Co. of Panama City, Fla.; and Res D-2083, available from Hercules; resins made from the polymerization and hydrogenation of a dicyclopentadiene feed stream such as Escorez 5380, available from Exxon; resins made from the polymerization and hydrogenation of a C9 hydrocarbon stream such as Arkon P-90, available from Arakawa Chemical Co. USA of Chicago, Ill.; and resins made from the polymerization and hydrogenation of mixtures of alphamethyl styrene, styrene, and vinyl toluene such as Regalrez 1065, Regalrez 1078, and Regalrez 1094, available from Hercules.

Conventional additives for hot-melt adhesives may also be incorporated into the bonding layer, including, but not limited to, waxes, fillers, oils, pigments, antioxidants, ultraviolet light stabilizers, and heat stabilizers.

The heat-activatable bonding layer may be applied to the mechanical engaging means in several ways preferably including extrusion-coating from a slot die of an extruder, or alternately by traditional solution coating, spray coating, transfer coating, or screen printing methods.

BRIEF DESCRIPTION OF DRAWING

The present invention will be further described with reference to the accompanying drawing wherein like reference numerals refer to like parts in the several views, and wherein.

DESCRIPTION OF THE PREFERRED EMBODIMENTS

Figure 1:
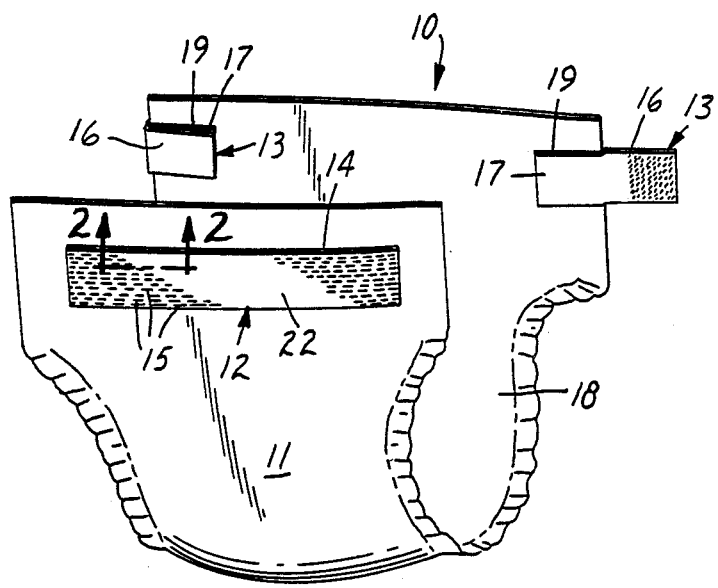
FIG. 1 is a perspective view of a disposable diaper according to the present invention.

Referring now to FIG. 1 there is shown a disposable garment or diaper according to the present invention generally designated by the reference numeral 10. The diaper 10 and an outer liquid-impermeable polyolefin film 11 included in the diaper 10 are generally rectangular in shape, and the diaper 10 includes a fastener portion 12 across what is intended to be the front of the diaper, and two fastener portions 13 adapted to engage end portions of the fastener portion 12 to hold the diaper 10 in place on a person wearing the diaper 10. The fastener portion 12 is elongate rectangular in shape (e.g., 20.3 centimeters long by 3.8 centimeters wide), is adhered by a bonding layer 14 having the properties described above to the outer film 11 over its entire length along one of the shorter sides of the rectangular diaper 10 with its length parallel to the short edge of the diaper 10, and has a multiplicity of loops 15 on its outer surface. The fastener portions 13 are supported on distal end portions of flexible elongate rectangular polymeric tabs 16 that have end portions 17 opposite the fastener portion 13 partly adhered both to inner edge portions of the outer film 11 and to an inner nonwoven polyolefin layer 18 of the diaper 10 by a bonding layer 19 having the properties described above. The fastener portions 13 include a multiplicity of hook like projections adapted to make releasable mechanical engagement with the loops 15 on the fastener portion 12 to afford attachment of the diaper 10 to a user such as an infant. The tabs 16 may have layers of low tack pressure-sensitive adhesive on portions of their surfaces opposite the film 11 and nonwoven layer 18 which allow the tabs 16 to be retained in a folded over condition (see the left tab 13 in FIG. 1) to protect the fastener portions 13 from chance unintentional engagement with various substrates prior to application of the diaper 10, at which time the tabs 16 may be easily peeled open (see the right tab 13 in FIG. 1) for engagement of the fastener portions 13 with end portions of the elongate fastener portion 12.

Figure 2:
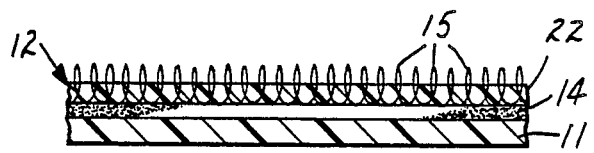
FIG. 2 is an enlarged sectional view taken approximately along line 2—2 of FIG. 1 which shows detail of a fastener portion and bonding layer incorporated in the diaper of FIG. 1.

As can be best seen in FIG. 2, the fastener portion 12 includes a backing layer 22 which could be a nonwoven material, but as illustrated is preferably a polymeric film (e.g., polyethylene), and has a plurality of through stitches formed with polymeric strands by a stitch-knitting machine such as the "Malimo" type Malipol Stitch-Knitting Machine manufactured by Textima in East Germany and distributed in the United Sates by Chima, Inc. of Reading, Pa., that form the multiplicity of loops 15 along its first surface adapted to be releasably mechanically engaged by the hooks on the mating fastener portions 13 (e.g., a length of the hook fastener material commercially designated Scotchmate Style sf-3491 available from Minnesota Mining and Manufacturing Company, St. Paul, Minn.). The bonding layer 14 is of room-temperature non-tacky thermoplastic material of the type described above, is adhered to a second major surface of the backing layer 22, and adheres the fastener portion 12 to the outer film 11 of the diaper 10. The thermoplastic resin in the bonding layer 18 was bonded to the polyolefin layer 11 under conditions of heat and pressure that left the polyolefin layer 11 substantially undeformed and with the bonding layer 18 holding the fastener portion 12 to the polyolefin film 11 with greater force than that which is required to separate the engaged fastener portions 12 and 13 so that the fastener portions 12 and 13 may be repetitively engaged and disengaged, and can also help to anchor the loops 15 in the backing layer 22.

Prior to being stitched to form the loops 15, the film backing layer 22 may be printed with one or more symbols, including written or pictorial instructional material, a brand name, or a pattern or design to improve the aesthetic appeal of the diaper 10 or to serve as indices that aid the user in fitting diapers onto an infant consistently from fitting to fitting. Such printing remains functionally visible through the loops 15.

Figure 3:
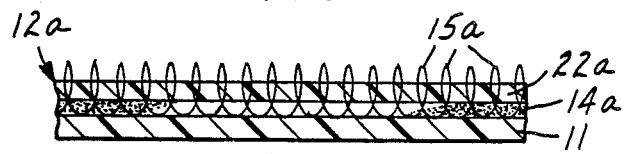
FIG. 3 is an enlarged sectional view of a first alternate embodiment of a fastener portion and bonding layer that can be incorporated in the diaper of FIG. 1.

FIG. 3 illustrates a first alternate embodiment of the fastener portion 12 and bonding layer 14 in which like parts are identified by the same reference numerals used in FIGS. 1 and 2 except for the addition of the suffix "a". The fastener portion 12a is the same as the fastener portion 12 shown in FIG. 2 except that a plurality of stitches of polymeric strands forming the multiplicity of loops 15a along a first surface to be releasably mechanically engaged by the hooks on the mating fastener portions 13 are stitched through both the backing layer 22a and the bonding layer 14a prior to adhering the fastener portion 12a to the outer film 11. The thermoplastic material in the bonding layer 14a helps to anchor the loops 15a, which anchoring occurred when the bonding layer 19a was adhered to the polyolefin layer 11 under heat and pressure that left the polyolefin layer 11 substantially undeformed. The portions of the stitches along the surface of the bonding layer 14a adjacent the film 11 did not prevent the formation of an acceptably secure bond between the bonding layer 14a and the polyolefin film 11.

Figure 4:
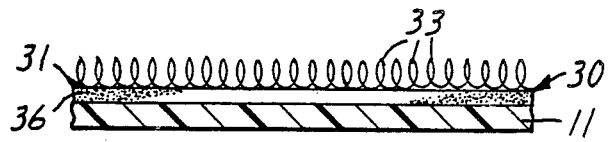
FIG. 4 is an enlarged sectional view of a second alternate embodiment of a fastener portion and bonding layer that can be incorporated in the diaper of FIG. 1.

Referring now to FIG. 4 there is shown a second alternate embodiment of a fastener portion 30 according to the present invention which includes a soft flexible sheet-like knitted or woven structure 31 comprising a multiplicity of loops 33 along a first surface (i.e., Samboo Plain Back Loop Fastener—210 Fastener (nylon) available from Samboo Ind. Co. Ltd., Seoul, South Korea), which loops are adapted to be releasably engaged by the mating fastener portions 13; and a bonding layer 36 of room-temperature non-tacky thermoplastic resin of the type described above adhered to a second major surface of the knitted structure that was bonded to the polymeric layer 11 under heat and pressure that left the polymeric film layer 11 substantially undeformed with the bonding layer holding the fastener portion 30 to the polymeric film 11 with greater force than that which is required to separate the portions 30 and 13 of the engaged fastener so that the portions 30 and 13 of the fastener may be repetitively engaged and disengaged.

Figure 5:
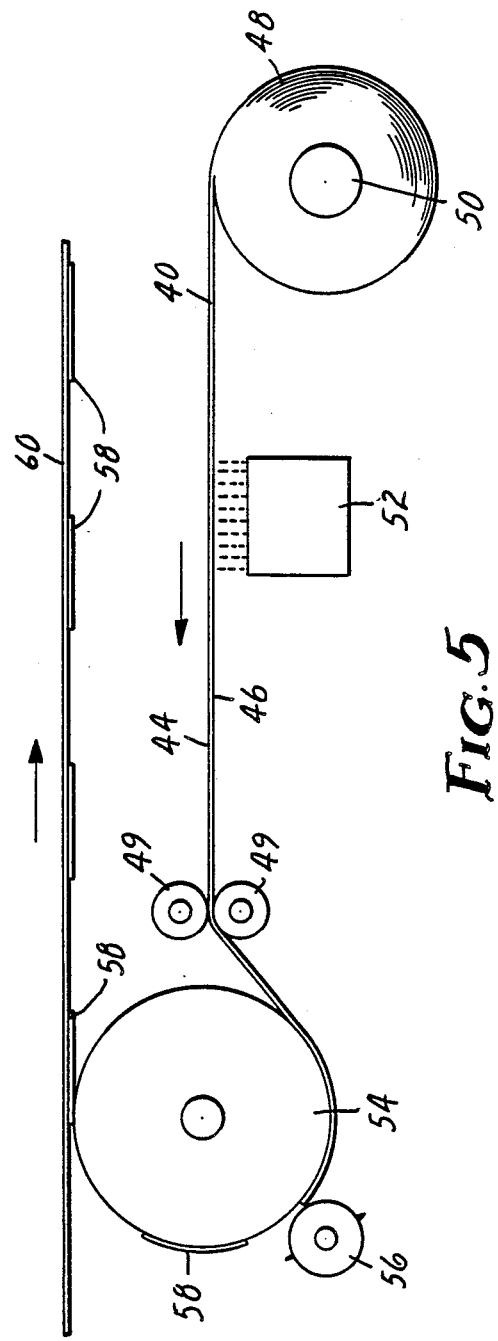
FIG. 5 schematically illustrates a method according to the present invention for applying fastener portions in a diaper manufacturing process.

FIG. 5 schematically illustrates a method for applying a preformed laminate 40 of a length of fastening material having mechanically engageable means such as loops along a first surface 44 and coated on its opposite second surface with a bonding layer 46 of room-temperature non-tacky thermoplastic resin of the type described above, which laminate 40 has no release coating on its first surface 44 and is rolled into a supply roll 48 without a release liner between its wraps. The laminate 40 is pulled at a predetermined rate by a pair of driven feed rollers 49 from the supply roll 48 which is mounted on a braked hub 50, and past a radiant heater 52 with the bonding layer 46 adjacent the heater 52 so that the bonding layer 46 is heated above its activation temperature. The heated laminate 40 propelled past the feed rollers 49 by the feed rollers 49 is held and slips against the surface of a vacuum drum 54 rotating at a peripheral speed greater than the rate of feed of the laminate 40 until a knife on a cutter wheel 56 engages and cuts a predetermined length 58 from the laminate 40 on the drum 54 so that the predetermined length 58 is carried by the drum 54 into engagement with a length of thin polyolefin film 60 moving at the same speed as the periphery of the vacuum drum 54 so that the still tacky bonding layer 46 on the predetermined length 58 will secure it to the polyolefin film 60 in a position spaced from the last applied predetermined length 58, after which the polyolefin film 60 may be further processed and incorporated with other materials to form finished diapers.

Peel Testing of Example Materials

Example Materials described below including lengths of various fastener portions having mechanically engageable means along first surfaces (or in some cases lengths of polymeric films that could be incorporated into such fastener portions) were coated on their opposite second surfaces with bonding layers of various room-temperature non-tacky thermoplastic materials. Several test samples were cut from each Example Material, and heated to different temperatures of 66, 88, and 110 degrees Centigrade (150, 190, and 230 degrees Fahrenheit) while their bonding layers were pressed at a pressure of 412 kPa (60 pounds per square inch) against polyethylene film of the type used as the outer layer of disposable diapers (i.e., 0.00325 centimeter (0.00128 inch) thick embossed polyethylene available as product number 103 from Consolidated Thermoplastics Co., Chippewa Falls, Wis., the bonding layers being applied against the male side of the embossing) which polyethylene film had a layer of pressure-sensitive adhesive tape (i.e., Scotch Brand 375-T, commercially available from Minnesota Mining and Manufacturing Company, St. Paul, Minn.) adhered to its side opposite the test samples to provide reinforcement for the polyethylene film somewhat similar to the reinforcement provided by the inner layers of a disposable diaper. 90 degree peel strength tests were then performed to determine the strengths of the bonds achieved between the bonding layers and polyethylene film, the results from which tests are tabulated in Table 1 below for the various Example Materials.

Specifically, each test sample was a 2.54 centimeter by 7.62 centimeter (1 inch by 3 inch) piece of one of the Example Materials. Each test sample was placed bonding layer up on a piece of silicone release paper. A 7.62 centimeter (3 inch) long end portion of a 2.54 centimeter by 16.5 centimeter (1 inch by 6.5 inch) piece of the pressure-sensitive adhesive tape backed polyethylene film was aligned along the bonding layer of the test sample, and a piece of ordinary notebook paper was positioned between the last 1.27 centimeter (0.5 inch) length of the bonding layer and the polyethylene film adjacent the end where the polyethylene/tape laminate extend beyond the bonding layer to provide an end portion of the fastener portion/bonding layer laminate for clamping onto the test jig described below of the peel strength test apparatus. A piece of silicone release paper was then positioned over the adhesive tape on the film, and the resulting structure was placed into a platen press heat sealer (i.e., a Sentinel Heat Sealer, Model 808, available from Packaging Industries Inc. of Hyannis, Mass.), and heated at one of the temperatures indicated above for a period of 3 seconds at a gauge pressure of 412 kPa (60 pounds per square inch) to form a test laminate. After at least a one half hour waiting period, the bond strength between the bonding layer and the polyethylene in the test laminate was tested by performing a 90 degree peel test in an Instron testing machine. The end portion of the fastener portion/bonding layer laminate provided by the notebook paper as described above and the opposite end portion of the fastener portion/bonding layer overlayed by the polyethylene/tape laminate were clamped with the polyethylene/tape laminate uppermost to a horizontal surface of a jig as described in PSTC-5 (incorporated herein by reference) held by the lower jaw of the Instron (to which surface a pressure sensitive adhesive coating on a tape is normally adhered in tests according to PSTC-5), the free end of the polyethylene/tape laminate was engaged by the upper jaw of the Instron, and the peel strength of the bond between the bonding layer and the polyethylene film was then determined as per PSTC-5, section 5.3.

To insure that a fastener portion will remain firmly adhered to a diaper through repeated closings and openings of the diaper fasteners, it is preferred that the strength of the bond between the bonding layer and the polyolefin layer of a diaper according to the present invention be in excess of the force required to tear the polyolefin layer which may be somewhat reinforced by being bonded to other layers of the diaper. The above peel strength test showed that the bond formed between the bonding layer and the polyethylene film was strong enough to distort or damage the tape reinforced polyethylene film at peel forces above 275.6 grams per centimeter (700 grams per inch) of width.

TABLE 1

| 90 Degree Peel Strength (grams per inch) for Bonding Temperatures Indicated | | | |
|---|---|---|---|
| Bonding Temperature | 66 C (150 F) | 88 C (190 F) | 110 C (230 F) |
| Example Material 1 | 2342* | 2283* | 2383* |
| Example Material 2 | 1600* | 2266* | 2183* |
| Example Material 3 | 2180* | 683* | 317** |
| Example Material 4 | 617** | 383** | 650** |
| Example Material 5 | 1917* | 2450* | 2617* |
| Example Material 6 | 600 | 2350* | 2717* |
| Example Material 7 | 467 | 1400* | 1433* |
| Example Material 8 | 633 | 900* | 1483* |
| Example Material 9 | 267 | 467 | 733* |
| Example Material 10 | 2510* | 2717* | 2717* |
| Example Material 11 | 1133 | 3133* | 2950* |

TABLE 1-continued

90 Degree Peel Strength (grams per inch)
for Bonding Temperatures Indicated

| Bonding Temperature | 66 C (150 F) | 88 C (190 F) | 110 C (230 F) |
|---|---|---|---|
| Example Material 12 | 1067* | 3500* | 3183* |

*failure occurred due either to stretching and tearing of the polyethylene in the polyethylene/tape laminate, or delamination of the pressure-sensitive adhesive tape from the polyethylene or tearing of the fastener portion/bonding layer laminate.
**the bonding layer separated from the fastener portion rather than from the polyethylene film.

Open Time Testing of Example Materials

The open time of the bonding layer, that is the time after separation from a heat source that heated the bonding layer to a temperature needed for activation that the bonding layer remains tacky even though the temperature of the bonding layer falls below its activation temperature by exposure to normal room temperature, was tested as described below for several of the different bonding layer compositions used in the various Example Materials by selecting one of the Example Materials using those compositions.

3.175 Centimeter by 10.2 centimeter (1.25 inch by 4 inch) test samples of the Example Materials tested were each placed bonding layer up on an about 15.24 centimeter by 25.4 centimeter (6 inch by 10 inch) piece of silicone release paper, and 1.27 centimeter (0.5 inch) at each end of the test sample was covered with a piece of pressure-sensitive adhesive tape to adhere the test sample to the release paper. The release paper with the attached test sample was placed in a circulating air convection oven for 2 minutes at 110 degrees Centigrade (230 degrees Fahrenheit). The sample was then quickly removed from the oven and placed on a lab bench at normal room conditions. At a predetermined time of either 3, 6, 9, or 30 seconds after removal of each test sample from the oven, a 2.54 centimeter by 15.24 centimeter (1 inch by 6 inch) piece of the polyethylene/tape laminate of the type described above was placed with the polyethylene in face-to-face contact with the bonding layer of the test sample and one end of the polyethylene/tape laminate aligned with one end of the test sample (resulting in 7.62 centimeters ((three inches)) of the polyethylene/tape laminate extending beyond the opposite end of the sample) and with a piece of paper positioned between the last 1.27 centimeter (0.5 inch) length of the bonding layer and the polyethylene film adjacent the extending end of the polyethylene/tape laminate to provide a clampable end portion of the fastener portion/bonding layer laminate as described above, and was quickly rolled down by two passes with a 2.04 kilogram (4.5 pound) hand roller to form a test laminate. Certain other test laminates including test samples of the same Example materials were prepared in the same manner except that the pieces of the polyethylene/tape laminate were applied in the manner indicated above while the sample was still in the oven resulting in 0 time between heating the bonding layer to its activating temperature and lamination of the bonding layer to the polyethylene. The 90 degree peel strength of the test laminates was tested on an Instron testing machine in the manner described above, the results from which tests are tabulated in Table 2 below for the various example materials tested.

TABLE 2

90 Degree Peel Strength (grams per inch) of Bonding Layer to Polyethylene for Various Periods of Time Between Heating the Bonding Layer and Lamination of the Bonding Layer to Polyethylene

| Seconds | 0 | 3 | 6 | 9 | 30 |
|---|---|---|---|---|---|
| Example Material 7 | 2200* | 1275* | 1925* | 1950* | 275 |
| Example Material 11 | 2200* | 2000* | 2250* | 1725* | 2150* |

*failure occurred due either to stretching and tearing of the polyethylene in the polyethylene/tape laminate, or delamination of the pressure-sensitive adhesive tape from the polyethylene or tearing of the fastener portion/bonding layer laminate.

EXAMPLE MATERIAL 1

A commercially available fastener material having a woven backing with loops along one surface (i.e., Samboo Plane Back Loop Fastener—210 Fastener (nylon) available from Samboo Ind. Co. Ltd., Seoul, South Korea) was extrusion-coated on the side opposite the loops with a composition consisting of 60 percent by weight of a random copolymer of ethylene and vinyl acetate having a melt flow index of 500 and a vinyl acetate content of 18% by weight (Elvax 410, available from E. I. DuPont de Nemours and Co. of Wilmington, Del.), and 40 percent by weight of a solid tackifying resin made from the polymerization and hydrogenation of a feed stream that is predominantly dicyclopentadiene having a softening point of 80 degrees Centigrade (Escorez 5380, available from Exxon Chemical Co.) to produce a bonding layer with a basis weight of 175 grams/square meter. The extrusion-coating was done on a single screw Haake Rheocord ¾" Extruder with a 25:1 L/D ratio, at a melt temperature of 90 degrees Centigrade and a line speed of 10 meters per minute.

EXAMPLE MATERIAL 2

A commercially available fastener material having a woven backing and stems projecting from a first side of the backing having mushroom shaped heads, (i.e., Scotchmate Style SF-3491, Available from Minnesota Mining and Manufacturing Company, St. Paul, Minn.) was extrusion-coated on the side opposite the projecting headed stems with the bonding layer composition and using the extruder and process conditions used to make Example Material 1 to produce a bonding layer having a basis weight of 150 grams per square meter.

EXAMPLE MATERIAL 3

A commercially available fastener material having a woven backing and loops projecting from a first side of the backing, (i.e., Velcro 1000-0199, available from Velcro USA, Inc., Manchester, N.H.) was extrusion-coated on the side opposite the loops with the bonding layer composition and using the extruder and process conditions used to make Example Material 1 to produce a bonding layer having a basis weight of 200 grams per square meter.

EXAMPLE MATERIAL 4

A commercially available fastener material having a woven backing and slit loops forming hooks projecting from a first side of the backing, (i.e., Velcro 080-0199, available from Velcro USA, Inc., Manchester, N.H.) was extrusion-coated on the side opposite the hooks with the bonding layer composition and using the extruder and process conditions used to make Example Material 1 to produce a bonding layer having a basis weight of 180 grams per square meter.

EXAMPLE MATERIAL 5

A polypropylene film about 45 microns thick and having a matte surface on both sides formed from polypropylene resin having a melt flow index of 35 (i.e., Escorene PP3085, available from Exxon Chemical Co., Houston, Tex.) which could be incorporated in a fastener material was extrusion-coated on one side with the bonding layer composition and using the extruder and process conditions used to produce Example Material 1 to produce a bonding layer having a basis weight of 150 grams per square meter.

EXAMPLE MATERIAL 6

A fastener material having loops projecting from one side was formed using polypropylene fibers commercially available as Style 80/2 with yarn size of 70/34 denier Solution-dyed Stuffer Crimped Olefin Fibers from Roselon Industries of New York, N.Y., and a conventional polypropylene film with a thickness of about 50 microns. The strands of polypropylene were passed through a comb having 6.3 teeth per centimeter (16 teeth per inch), and were then fed between a pair of meshing crimping spur gears with teeth parallel to their axes and were carried by one of the spur gears into engagement with the film moving at the same rate as the outer surface of the teeth on that spur gear. The portions of the strands on the tips of the teeth brought into engagement with the polypropylene film were sonically welded to the polypropylene film resulting in a fastening material having weld lines perpendicular to the strands and to the direction of movement of the polypropylene film each approximately 0.159 centimeter (0.0625 inches) in width and spaced 0.318 centimeter (0.125 inches) apart. The teeth of the gears were shaped so that the feed rate of the strands in length per unit time was about 1.5 times that of the bilayered film, resulting in projecting loops roughly semicircular in shape with radii of about 0.318 centimeter (0.125 inch). The fastener portion thus formed was extrusion-coated on its side opposite the loops with the bonding layer composition and using the extruder and process conditions used to make Example Material 1 to produce a bonding layer having a basis weight of 80 grams per square meter.

EXAMPLE MATERIAL 7

A fastener material having loops projecting from one side was prepared by stitching through a 45 micron thick high density polyethylene film, commercially available as HMHDPE 0.00445 centimeter (1.75 mil) thick Polyethylene from W.B.C. Extrusion Products Inc., Lowell, Mass. using a "Malimo" (TM) Sewing-knitting machine set at 3.9 courses per centimeter (10 courses per inch) and 5.5 wales per centimeter (14 wales per inch), the stitches being made using 70 denier 34 strand texturized polyester yarn commercially available from Unifi Inc., Greensboro, N.C., to produce a fastener material having an overall basis weight of about 60 grams/square meter. The fastener portion thus formed was extrusion-coated on its side opposite the loops with the bonding layer composition and using the extruder and process conditions used to make Example Material 1 to produce a bonding layer having a basis weight of 245 grams per square meter.

EXAMPLE MATERIAL 8

A fastener material formed the same way as the fastener material for Example Material 7 was extrusion coated on its side opposite the loops with a composition consisting of 60 percent by weight of a random copolymer of ethylene and vinyl acetate having a melt flow index of 500 and a vinyl acetate content of 18% by weight (Elvax 410, available from DuPont), and 40 percent by weight of a synthetic hydrocarbon solid tackifying resin with a softening point of 95 degrees Centigrade (Escorez 1310 LC, available from Exxon Chemical Co., Houston, Tex.) using the extruder and process conditions used to form Example Material 1 to produce a bonding layer having a basis weight of 200 grams per square meter.

EXAMPLE MATERIAL 9

A fastener material having loops projecting from one side was prepared by forming a bilayer film by first extruding a 40 micron thick cast polypropylene film using a conventional polypropylene material having a melt flow index of 35, (i.e., Escorene PP3085, commercially available from Exxon Chemical Co., Houston, Tex.) and then extrusion-coating a bonding layer consisting of 80 percent by weight of a random copolymer of ethylene and vinyl acetate having a melt flow index of 57 and a vinyl acetate content of 40% by weight (Elvax 40W, available from DuPont), and 20 percent by weight of a solid tackifying resin made from the polymerization and hydrogenation of a feed stream that is predominantly dicyclopentadiene having a softening point of 80 degrees Centigrade (Escorez 5380, available from Exxon Chemical Co., Houston, Tex.) onto the polypropylene film using extruder conditions similar to those used to form Example Material 1 to produce a bonding layer having a basis weight of 25 grams per square meter. The bilayer film was then stitched through both of the layers to form the loops using the same "Malimo" (TM) Sewing-knitting machine, settings and yarn indicated for Example Material 7.

EXAMPLE MATERIAL 10

A commercially available fastener material having a woven backing and stems projecting from a first side of the backing having mushroom shaped heads on their distal ends, (i.e., Scotchmate Style sf-3491, available from Minnesota Mining and Manufacturing Company, St. Paul, Minn.) was laminated on its side opposite the projecting headed stems with a bonding layer formed as follows. A composition consisting of 60 percent by weight of a random copolymer of ethylene and vinyl acetate having a melt flow index of 400 and a vinyl acetate content of 33% by weight (Elvax 4980W, available from DuPont), and 40 percent by weight of Escorez 5380 was extruded through the extruder used to form Example Material 1, and the molten extrudate was collected in an aluminum pan. After the extrudate had cooled, a piece of the extrudate weighing about 5 grams was cut away, had a layer of silicone release paper positioned on both sides, was placed in a platen press (Sentinel Heat Sealer, Model 808, available from Packaging Industries Inc. of Hyannis, Mass.), and was pressed at a gauge pressure of 618 kPA (90 psi) while being heated at temperature of 204 degrees Centigrade (400 degrees Fahrenheit) by the press for 10 seconds to produce a film with a basis weight of 340 grams per square meter. After this pressed film had cooled for several minutes it was removed from the silicone release papers, a 2.54 centimeter (1 inch) by 7.62 centimeter (3 inch) piece of the fastener material was placed on a piece of silicone release paper with its side opposite its projecting headed stems facing up, and a 2.54 centimeter (1 inch) by 7.62 centimeter (3 inch) piece of the pressed film was placed on top of the fastener material. A second piece of silicone release paper was placed on top of the piece of pressed film, and the resulting composite was placed in the same platen press used to make the film and pressed at a pressure of 618 kPA (90 psi) while being heated at a temperature of 204 degrees Centigrade (400 degrees Fahrenheit) by the press for 10 seconds. The composite was then removed from the press, allowed to cool to room temperature, and the release papers were removed leaving Example Material 10.

EXAMPLE MATERIAL 11

A commercially available fastener material having a woven backing and loops projecting from a first side of the backing, (i.e., Samboo Plane Back Loop Fastener—210 Fastener (nylon) available from Samboo Ind. Co. Ltd., Seoul, South Korea) was laminated on its side opposite the projecting loops in the same manner and to the same bonding layer described for Example Material 10 to form a bonding layer having a basis weight of 130 grams per square meter.

EXAMPLE MATERIAL 12

A polypropylene film about 45 microns thick and having a matte surface on both sides formed from polypropylene resin having a melt flow index of 35 (i.e., Escorene PP3085, available from Exxon Chemical Co., Houston, Tex.) which could be incorporated in a fastener material was laminated to the same bonding layer in the same manner described to form Example Material 10 to form a bonding layer having a basis weight of 150 grams/square meter.

GENERAL

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

We claim:

1. A disposable diaper or similar disposable garment comprising a heat and pressure-sensitive polyolefin layer,
   a fastener including fastener portions having first and second major surfaces, a multiplicity of hook like projections along the first surface of one of said fastener portions, and a multiplicity of projecting members along the first surface of the other of said fastener portions adapted for releasable mechanical engagement by said hook like projections; and
   a bonding layer of room-temperature non-tacky thermoplastic material adhering the second surface of at least one of said fastener portions to said polyolefin layer and being bonded to the polyolefin layer under heat and pressure that leaves the polyolefin layer substantially undeformed due to melting or distortion,
   the bonding layer holding the fastener portion to the polyolefin film with greater force than that which is required to separate the engaged fastener so that the fastener may be repetitively closed and opened.

2. A diaper or similar disposable garment according to claim 1 wherein the bonding layer holding the fastener portion to the polyolefin film with greater force than that which is required to deform the polyolefin layer when a 90 degree peel test is performed between the polyolefin film and the bonding layer.

3. A diaper or similar disposable garment according to claim 1 wherein the polyolefin layer is a film less than 0.005 centimeter (0.002 inch) thick, and said bonding layer bonds said fastener portion to said film to produce a 90 degree peel strength of at least 118 gram per centimeter (300 grams per inch).

4. A diaper or similar disposable garment according to claim 1 wherein the bonding layer includes from about 40% to about 100% of a thermoplastic material having an softening point of generally below 120 degrees Centigrade, and from about 60% to about 0% of a tackifying resin that has a softening point below about 105 degrees Centigrade.

5. A diaper or similar disposable garment according to claim 1 wherein the bonding layer includes from about 40% to about 90% of a thermoplastic material having an softening point of generally below 100 degrees Centigrade, and from about 60% to about 10% of a tackifying resin that has a softening point below about 95 degrees Centigrade.

6. A diaper or similar disposable garment according to claim 5 wherein said thermoplastic material is a copolymer of ethylene and vinyl acetate having a melt flow index between about 50 and about 2500.

7. A diaper or similar disposable garment according to claim 1 wherein the bonding layer has an activation temperature of below generally 110 degrees Centigrade.

8. A diaper or similar disposable garment according to claim 1 wherein the bonding layer has an activation temperature of below generally 100 degrees Centigrade, and said bonding layer has an open time of over 2 seconds at room temperature after being removed from heat that has heated said bonding layer to said activation temperature.

* * * * *